(12) United States Patent
Kopta et al.

(10) Patent No.: US 10,224,760 B2
(45) Date of Patent: Mar. 5, 2019

(54) SYSTEM AND METHOD FOR REMOTE POWERING AT LEAST ONE SENSOR OR ACTUATOR FROM A RF POWER SOURCE

(71) Applicant: CSEM Centre Suisse d'Electronique et de Microtechnique SA—Recherche et Developpement, Neuchatel (CH)

(72) Inventors: Vladimir Kopta, Neuchatel (CH); John Farserotu, Vesenaz (CH); Oleksandr Vorobyov, Peseux (CH)

(73) Assignee: CSEM CENTRE SUISSE D'ELECTRONIQUE ET DE MICROTECHNIQUE SA—RECHERCHE ET DÉVELOPPEMENT, Neuchatel (CH)

(*) Notice: Subject to any disclaimer, the term of this patent is extended or adjusted under 35 U.S.C. 154(b) by 179 days.

(21) Appl. No.: 15/336,955

(22) Filed: Oct. 28, 2016

(65) Prior Publication Data
US 2017/0126073 A1    May 4, 2017

(30) Foreign Application Priority Data
Oct. 29, 2015 (EP) ..................................... 15192228

(51) Int. Cl.
| | |
|---|---|
| *H02J 50/27* | (2016.01) |
| *H02J 50/40* | (2016.01) |
| *H02J 50/20* | (2016.01) |
| *H01P 3/16* | (2006.01) |
| *H02M 7/02* | (2006.01) |
| *H01P 3/12* | (2006.01) |
| *H01P 3/14* | (2006.01) |
| *A61B 18/18* | (2006.01) |
| *A61B 18/00* | (2006.01) |
| *H01Q 13/22* | (2006.01) |

(52) U.S. Cl.
CPC .............. *H02J 50/27* (2016.02); *H01P 3/121* (2013.01); *H01P 3/14* (2013.01); *H01P 3/165* (2013.01); *H02J 50/20* (2016.02); *H02J 50/40* (2016.02); *H02M 7/02* (2013.01); *A61B 18/1815* (2013.01); *A61B 2018/0088* (2013.01); *A61B 2018/00791* (2013.01); *H01Q 13/22* (2013.01)

(58) Field of Classification Search
CPC ....................................................... H02J 50/27
USPC ......................................................... 307/104
See application file for complete search history.

(56) References Cited

U.S. PATENT DOCUMENTS

| | | |
|---|---|---|
| 5,031,980 A | 7/1991 | Colles et al. |
| 8,390,402 B2 | 3/2013 | Kunes |
| 2006/0165360 A1 | 7/2006 | Siegel et al. |

(Continued)

OTHER PUBLICATIONS

European Search Report dated Apr. 6, 2016 for EP15192228.

*Primary Examiner* — Joseph Chang
(74) *Attorney, Agent, or Firm* — Pearne & Gordon LLP

(57) ABSTRACT

A system for remote powering at least one sensor or actuator from a RF power source including a flexible waveguide having a flexible dielectric layer and at least one flexible conductive layer connected to the flexible dielectric layer. The at least one sensor or actuator is arranged to be coupled to the flexible waveguide and the RF power source is arranged to be wirelessly coupled to the flexible waveguide and to generate RF power. The flexible waveguide guides the propagation of the RF power from the RF power source to the sensor or actuator in order to wirelessly power the sensor or actuator.

18 Claims, 2 Drawing Sheets

(56) References Cited

U.S. PATENT DOCUMENTS

| | | | |
|---|---|---|---|
| 2011/0160542 A1* | 6/2011 | Ahn | H02J 50/27 |
| | | | 600/300 |
| 2014/0240187 A1 | 8/2014 | Herbsommer et al. | |
| 2015/0042522 A1 | 2/2015 | Laifenfeld et al. | |
| 2015/0141981 A1 | 5/2015 | Price et al. | |

* cited by examiner

SYSTEM AND METHOD FOR REMOTE POWERING AT LEAST ONE SENSOR OR ACTUATOR FROM A RF POWER SOURCE

FIELD

The present invention concerns a system and a method for powering at least one sensor or at least one actuator from a RF power source.

DESCRIPTION OF RELATED ART

A waveguide is a structure used for guiding a wave, e.g. an electromagnetic wave, from a first point to a second point, e.g. from a first end to a second end of the waveguide. This wave is in general a signal conveying information between the endpoints of the waveguide. Therefore, a waveguide is in general a structure used for transmitting an information signal generated from a signal source to a signal receiver, both the source and the receiver being in general external to the waveguide, and coupled to the waveguide, e.g. by a direct contact with the waveguide.

There are different types of waveguides depending on the type of wave to convey. The most common waveguide is a hollow conductive metal pipe used to carry high frequency radio waves, in particular microwaves. As known, the geometry of the waveguide can vary, depending on its application.

A waveguide can also be created on a printed circuit board. In such a case, it employs a solid dielectric core rather than a hollow pipe.

Transmission lines can be created on a printed circuit board too. An example of a transmission line on a printed circuit board is the microstrip, used to convey microwave-frequency signals and comprising a conducting strip separated from a ground plane by a dielectric layer. As microstrips are not enclosed, they have some drawbacks as e.g. higher losses, cross-talking, unintentional radiation, etc.

Other examples of transmission lines on a printed circuit board are striplines and coplanar waveguides.

The state of the art comprises different examples of flexible waveguides (hollow pipe waveguide or printed waveguide) for different applications, e.g. medical or surgical applications, or satellite communication applications.

For example, US20060165360 describes a RF waveguide targeted between 300 GHz and 30 THz and comprising a hollow core and a flexible honeycomb periodic-bandgap structure surrounding the hollow core. This structure comprises a plurality of tubes having approximately equal size. The described waveguide is a low loss waveguide (less than 1 dB per meter) and it is used in a fiberscope: a beam-splitter is located within the waveguide for polarising a signal passing through the waveguide and a signal receiver is coupled with the beam splitter to receive a reflected signal. The structure is complex and the hollow core needs to have a circular cross-section.

US2015141981 describes a surgical instrument system in which ultrasound or RF energy is conveyed to a tissue for cutting and/or coagulation purposes via an electrode surface adjacent to the tissue. The energy is delivered from the generator to this electrode surface via one or more conductors. Therefore, it is necessary a mechanical contact between the generator and the electrode surface.

U.S. Pat. No. 5,031,980 describes an optical waveguide for transmitting infrared and visible light for surgical applications. The waveguide comprises a flexible waveguide for infrared radiation comprising a series of alumina tubes spaced apart by axial gaps and held within a flexible plastics sleeve. An optical fibre suitable for transmitting visible light is arranged in a helical path around the sleeve. The assembly of flexible waveguide, sleeve and fibre is enclosed in an outer plastics covering. This assembly is complex and voluminous.

U.S. Pat. No. 8,390,402 describes a flexible waveguide for an on-board satellite communication application. The waveguide comprises a dielectric inner region and an electrically conducting outer region spaced apart from the dielectric inner region. The flexibility is achieved by forming this dielectric inner region from powdered dielectric contained in a polymer tube or matrix, or from a plurality of segments. Spacers are necessary for maintaining a separation between the dielectric core and the electrically conducting outer region even when the waveguide is bent. The waveguide is used for guiding an electromagnetic radiation signal having a microwave length from a component like an amplifier, filter, multiplexer, etc. to the next, so as to retransmit a processed signal.

US20140240187 describes a dielectric waveguide having a mating end configured in a non-planar shape for mating with another dielectric waveguide having a non-planar shaped mating end. Cables or wires provide power the dielectric waveguide.

In all the previous examples, if a power source is present for powering purposes, i.e. for providing to a device or in general to a node the energy that it needs in order to work, this energy is transmitted to the device or node via a conductor connected at one side to the power source and on the other side to the device or node to power.

The applicant was confronted to the problem of easily placing and powering at least one node or device (e.g. a sensor or an actuator) on a target. In particular, the applicant was confronted to the problem of easily placing and powering a plurality of such nodes. Those nodes are used for different applications, e.g. for medical purposes (they can be e.g. sensors on a part of a human body, on a prosthesis, on an exoskeleton, on a catheter, etc.), for construction purposes (e.g. sensors on a wall, on a pipe, etc.), for automotive purposes (e.g. sensors or actuators on a tire, motor, etc.), for industry purposes (e.g. sensors or actuators on an industrial robot or machine), etc.

The powering is in general performed from a RF power source. In the context of the present invention, the expression "RF power source" designates a source generating a power having a frequency belonging to the range from 1 MHz to several hundred GHz (sub-THz), in particular in the range from 1 MHz to 100 GHz, in particular in the range from 1 GHz to 10 GHz, for example 2.4 GHz.

The applicant found that the use of wires or mechanical contacts between the power source and the device or node to be powered can be difficult to implement and could be a source of failure. Moreover, wires or mechanical contacts could raise manufacturing costs and complexity. Finally, they can constrain the position of the nodes to be powered.

SUMMARY

Therefore, it is an aim of the present invention to propose a system for powering at least one sensor or at least one actuator from a RF power source simple to implement.

It is an aim of the present invention to propose a system for powering at least one sensor or at least one actuator from a RF power source having a cost lower than known solution.

It is an aim of the present invention to propose a system for powering at least one sensor or at least one actuator from a RF power source in which the positions of the sensors or of the actuators are not constrained for powering purposes.

It is an aim of the present invention to propose a system for powering at least one sensor or at least one actuator from a RF power source, which can be easily placed on a target having different shapes and various contours. In other words, it is an aim of the present invention to propose a system for powering at least one sensor or at least one actuator from a RF power source, which is standalone and self-standing.

According to the invention, these aims are achieved by means of a system for remote powering at least one node, the node being a device as a sensor or an actuator, from a RF power source, comprising a flexible waveguide comprising
a flexible dielectric layer and at least one flexible conductive layer connected to this flexible dielectric layer,
at least one node arranged to be coupled to the flexible waveguide,
the RF power source, which is arranged to be wirelessly coupled to the flexible waveguide and to generate RF power.

In the context of the present invention, the adjective "flexible" referred to a waveguide and to the dielectric and conductive layers, means that the waveguide respectively the layers can be bent without breaking.

For example, the dielectric layer can be made by flexible plastic substrates, such as polyimide, PET or silicone. The conductive layer can be made e.g. by a copper foil or by a coating (i.e. performed by the Aerosol Jet technology) comprising a conductive alloy or any other flexible metal or alloy. In one embodiment, the conductive layer comprises or is made of liquid metal. In another embodiment, it comprises or is made of carbon-based materials.

In a preferred embodiment, the dielectric and conductive layers are also stretchable, i.e. they are made or be capable of being made longer or wider without tearing or breaking. For example the dielectric layer can be made by stretchable materials such as silicones or polyurethanes, and the conductive layer by carbon-based materials.

In another embodiment, they are also elastic, i.e. the can be easily return to their original size or shape after being stretched or otherwise deformed.

According to the invention, the flexible waveguide is arranged for the guided propagation of the RF power from the RF power source to the node or nodes in order to power the node(s) in a contactless way, as there is no contact between the source and the node(s).

In other words, the system according to the invention is devoid of a galvanic connection between the node(s) and the RF power source, as well as between the node(s) and the conductive layer(s) of the flexible waveguide.

Therefore, the system according to the invention allows the remote powering of nodes or devices via guided propagation of RF energy through a flexible waveguide structure. The proposed solution eliminates then the need for batteries as well as the need for contacts and wires for powering or connecting nodes.

The system according to the invention is therefore robust and easy and cheap to manufacture.

The sensor(s) according to the invention are devices which—once powered—detect or measure a physical property and record, indicate, or otherwise respond to it. Examples of such sensors are temperature sensors, pressure sensors, humidity sensors, position sensors, acceleration sensors, orientation sensors, vibration sensors, stress sensors, etc. They can also use different technologies and be e.g. inductive sensors, capacitive sensors, Hall sensors, magnetoresitive sensors, etc.

In one preferred embodiment, the sensors are arranged to associate a time stamp and/or a location information to the detected or measured physical property.

The actuator(s) according to the invention, once powered, make a machine or a device operate, by converting energy in motion. Examples of actuators comprise micro-motors, piezoelectric actuators, electroactive polymers, biomorph, camera's actuators, etc.

In one preferred embodiment, the node (e.g. the sensor or actuator) comprises a RF/DC power converter arranged to convert the received RF power from the RF power source via the flexible waveguide to a DC power, which is sent to a DC power supply module connected to the converter.

In another embodiment, the node is an ultra-low power node, e.g. a node suitable to be powered with RF power of some tens of mW or less. In one preferred embodiment, the nodes operate via energy harvesting, as they derive energy from the RF power source.

In the context of the present invention, the expression "dielectric layer" indicates a layer made by a dielectric, i.e. an electrical insulator that can be polarized by an applied electric field.

In the context of the present invention, the expression "conductive layer" indicates a layer capable of conducting electrical energy. It designates a physical layer, or a mesh, or a bunch of parallel conductors. In one preferred embodiment, the conductive layer comprises or it is made of a flexible metal, e.g. copper-silver based. In another embodiment, it comprises or it is made of Indium tin oxide (ITO), zinc oxide (ZnO). In another embodiment it comprises or it is made of a coating (i.e. performed by the Aerosol Jet technology) comprising a conductive alloy or any other flexible metal or alloy, or any other non-metallic flexible material having electrical conductivity. In one embodiment, the conductive layer comprises or is made of liquid metal. In one embodiment, the conductive layer comprises or is made of carbon-based materials. In another embodiment, it comprises one or more antennas.

In the context of the present invention, the expression "the sensor or the actuator is arranged to be coupled to the flexible waveguide" indicates that the sensor or the actuator can be inside or outside the flexible waveguide.

In one preferred embodiment, the node is in the flexible dielectric layer, so in the flexible waveguide: in such a case, the node is powered by the power wirelessly conveyed by the flexible waveguide, in particular by its dielectric layer.

In another embodiment, the node is outside the waveguide: in such a case, the waveguide comprises an antenna (distinct from the antenna of the RF power source) for transmitting the RF power from the RF power source to the node. In such a case, the node must be placed at a distance from this antenna, allowing the reception by the node of at least the minimum power necessary to the node for working. For example, the node can be placed in the near field of this antenna.

In one preferred embodiment, the antenna is a slot antenna formed in the conductive layer of the waveguide. As the conductive layer is flexible, the antenna will be flexible as well. If the conductive layer is also stretchable and/or elastic, the antenna will be stretchable and/or elastic as well.

In the context of the present invention, the expression "the power source is arranged to be wirelessly coupled to the flexible waveguide" indicates that the RF power source can be inside or outside the flexible waveguide, and that there exists a wireless coupling between the RF power source and the flexible waveguide, allowing the power from the RF power source to be distributed by the flexible waveguide.

In one preferred embodiment, the RF power source is in the flexible dielectric layer: in such a case, the flexible waveguide itself acts as a power source, distribution and delivery system.

In another embodiment, the RF power source is placed outside the waveguide but not in direct contact with the waveguide. For example, the waveguide can be in near field of the RF power source, i.e. in the region in which the oscillation of the field generated by the source can be approximated by a spherical wave.

In other words, the RF power source is in proximity to the flexible waveguide, so that the wireless transmission of the power from RF power source to the flexible waveguide can be efficiently achieved. For example, the RF power source emitting a power with a frequency of 2.4 GHz is placed at a distance of a few millimetres to a few tens of centimetres from the flexible waveguide.

In one preferred embodiment, the flexible waveguide forms a flexible sheet device. The expression "sheet device" in the context of the present invention designates a device, in particular a flat or planar device, in which the sizes along the x and y axes are at least one order of magnitude larger than the size along the z axis. In other words, the flexible waveguide according to the invention is substantially bi-dimensional, i.e. the power can propagate with two independent propagation directions. In one preferred embodiment, the sizes along the x and y axes are of the same order of magnitude.

The flexible sheet device can have a rectangular, squared, circular, oval or polygonal shape, or any other regular or irregular shapes.

In one preferred embodiment, for a RF power source of 2.4 GHz and medical or construction applications, the thickness of the flexible waveguide is less than 5 mm, e.g. 1 mm. However, the thickness of the flexible waveguide could vary with potential applications and frequency of operation.

The system comprising the flexible sheet device is stand-alone and self-standing, and can be easily placed on a target and can conform to the surface of the target thanks to its flexibility. Here the term "target" should be understood as a receiving device which can receive the flexible sheet device. Such receiving device can include a receiving device for medical purposes (e.g. a human or animal body, a prosthesis, an exoskeleton, a catheter, etc.), a receiving device for building applications (e.g. a wall, a pipe, etc.), a receiving device for automotive purposes (e.g. sensors or actuators on a tire, motor, etc.), a receiving device for industry purposes (e.g. sensors or actuators on an industrial robot or machine), etc., or a receiving device for any other suitable applications. It can take different shapes and various contours depending on the application. Moreover, it can also be stretchable.

In one embodiment, the flexible sheet device according to the invention is rolled around a tube or pipe.

In one preferred embodiment, the flexible sheet device is an artificial skin that can be used for prosthetics exoskeletons, tactile service and industrial robots able to work around people, as e.g. cyber skin.

In one preferred embodiment, the flexible sheet device comprises connecting means allowing to perform a mechanical connection, preferably a removable connection, with the target on which it is placed. Examples of such connecting means comprises glue, adhesive, Velcro®, belt, strip, etc.

The present invention concerns also a method for remote powering at least one sensor or actuator from a RF power source, comprising
generating a RF power from the RF power source, this RF power source being wirelessly coupled to a flexible waveguide, the flexible waveguide comprising a flexible dielectric layer and at least one flexible conductive layer,
guiding the propagation of the RF power or guiding the RF power from the RF power source to the at least one sensor or actuator, the at least one sensor or actuator being coupled to the flexible waveguide,
receiving the RF power by the at least one sensor or actuator, and
powering the at least one sensor or actuator by using the RF power, e.g. by converting the RF power to DC power.

The present invention concerns also the use of a flexible waveguide comprising a flexible dielectric layer and at least one flexible conductive layer, for the guided propagation of a RF power from a RF power source arranged to be wirelessly coupled to the flexible waveguide, to at least one sensor or actuator arranged to be coupled to the flexible waveguide, in order to wirelessly power this sensor or actuator.

BRIEF DESCRIPTION OF THE DRAWINGS

The invention will be better understood with the aid of the description of an embodiment given by way of example and illustrated by the Figures, in which.

DETAILED DESCRIPTION OF POSSIBLE EMBODIMENTS

Figure 1:
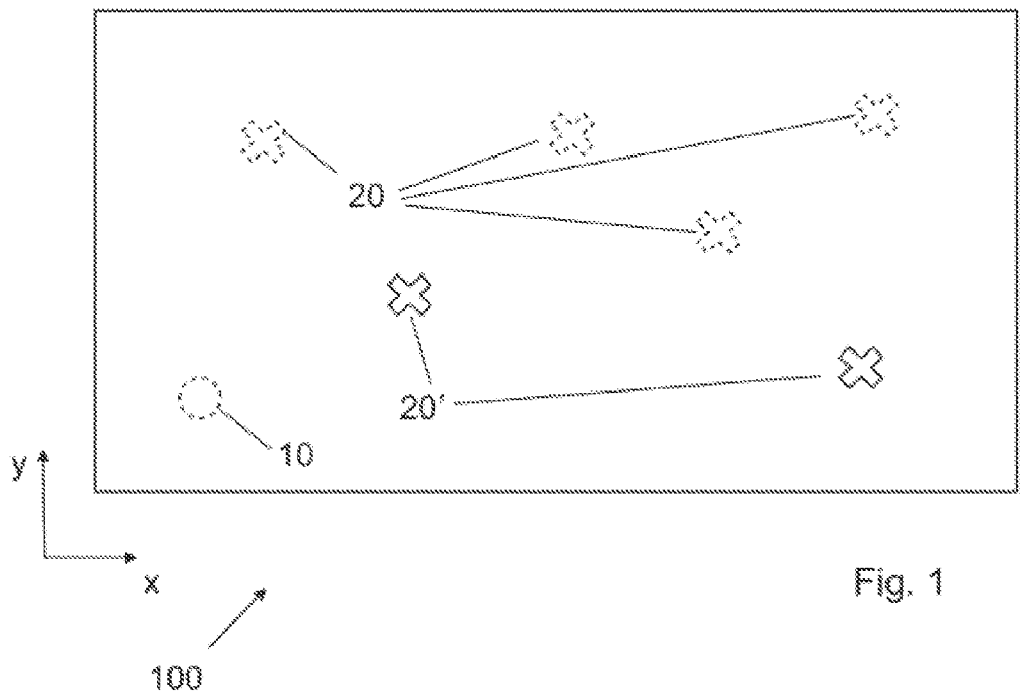
FIG. 1 shows a top view of a first embodiment of the system comprising a flexible waveguide comprising nodes, according to an embodiment.
Figure 2:
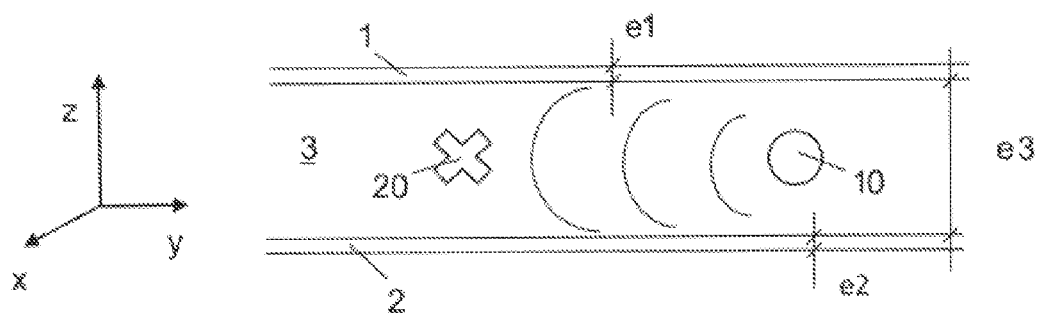
FIG. 2 shows a section view of the system according to an embodiment.
Figure 3:
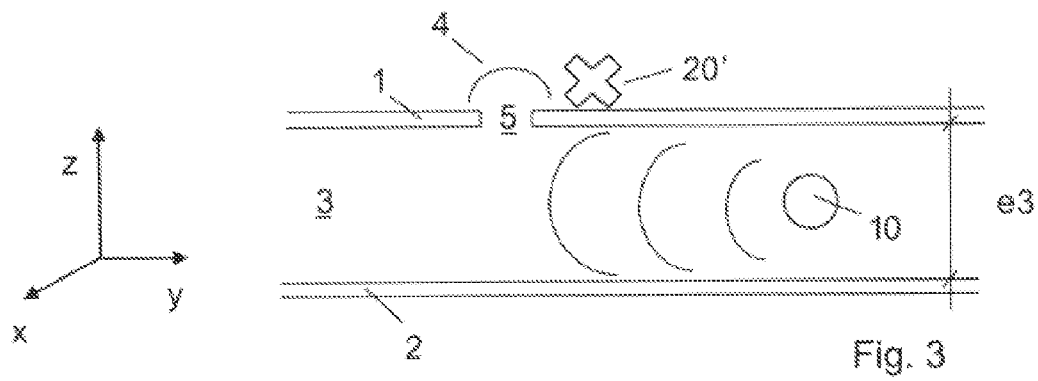
FIG. 3 shows a section view of the system according to another embodiment.

FIG. 1 shows a top view of a first embodiment of the system 100 according to the invention. The system 100 comprises a flexible waveguide, better visible on FIGS. 2 and 3. In the embodiments of FIGS. 2 and 3 it comprises a first flexible conductive layer 1, a second flexible conductive layer 2 and a flexible dielectric layer 3 in between the first and second conductive layers 1, 2.

The "dielectric layer" is in this context a layer made by a dielectric, i.e. an electrical insulator that can be polarized by an applied electric field.

The conductive layers 2 and 3 are in the illustrated embodiments two identical metallic layers. However, they can be made by different materials. Moreover the present invention is not limited to metallic layers, but covers also conductive layers comprising a mesh or a bunch of parallel conductors.

Although the flexible waveguide of FIGS. 2, 3 is made of a sandwich of a first flexible conductive layer 1, a flexible dielectric layer 3 and a second conductive layer 2, it must be understood that the present invention is not limited to the presence of two flexible conductive layers 1, 2, and that it can work with only one flexible conductive layer 1 or 2.

In a variant, the flexible waveguide can comprise only the flexible dielectric layer 3; in other words, the dielectric waveguide is used without a metallic surface.

However, the two flexible conductive layers 1, 2 allow a more efficient guided propagation in the flexible dielectric layer 3 of the RF power signal generated by the RF power source.

In one preferred embodiment, the flexible waveguide is realised on a PCB (Printed Circuit Board), in particular on a flexible PCB.

The system according to the invention comprises a RF power source 10. In the embodiments of FIGS. 1 to 3, the RF power source 10 is placed in the flexible dielectric layer 3, so it is inside the flexible waveguide (for this reason it has been represented with dotted lines on FIG. 1).

The RF power source 10 is a source generating a power having a frequency belonging to the range from 1 MHz to several hundred GHz (sub-THz), in particular to the range from 1 MHz to 100 GHz, in particular to the range from 1 GHz to 10 GHz, for example 2.4 GHz. It is a wireless power source. In one preferred embodiment, the RF power source is a Bluetooth power source, generating e.g. a power of about 100 mW with a frequency of 2.4 GHz.

The flexible waveguide is designed so that it can guide the propagation of the power or guide the power generated by the RF power source 10 in the flexible dielectric layer 3. For example, the thickness of the conductive layers 1, 2 is higher than the skin depth, which mainly depends on the frequency of the power signal and on the material of the conductive layers 1, 2. For example, the thickness e1 and e2 of metallic conductive layers 1 respectively 2 is in the range of 2 µm to 100 µm for a frequency of the RF power of 2.4 GHz. If the thickness e1 and e2 of metallic conductive layers 1 respectively 2 are sensibly lower than 2 µm, e.g. 0.02 µm, the corresponding layers will have low conductive properties and their use in the system according to the invention will be not efficient. Layers of such low thickness, fabricated e.g. by using vacuum metallization techniques, can be used mainly for corrosion protection.

The thickness e3 of the flexible dielectric layer 3 is in one embodiment in the range of 1 mm to 3 mm. However, its thickness could vary with potential applications and frequency of operation. We note that, as the dielectric layer 3 is flexible, the bigger the thickness e3, the lower the flexibility of the layer 3.

The three layers 1 to 3 are then superposed, and have substantially the same size and shape. In the embodiment of FIG. 1, they have a rectangular shape and form a flexible sheet device. In particular, the sizes along the x and y axes of the flexible waveguide of FIG. 1 are at least one order the magnitude bigger than the size along the z axis, i.e. than the total thickness e1+e3+e2 of the flexible waveguide. For example, for a total thickness e1+e3+e2 of the flexible waveguide of less than 5 mm, the sizes along the x and y axes of the flexible waveguide of FIG. 1 can be of the order of magnitude of about 5 cm to 10 cm for a medical application, e.g. for being placed on a hand of a patient.

Therefore, the flexible waveguide according to the invention is substantially bi-dimensional, i.e. the power can propagate with two independent propagation directions.

Of course, the flexible sheet device is not limited to a rectangular shape and can have other type of shapes, regular or irregular.

The flexible sheet device according to the invention can be coupled with at least one node 20, 20'. The term "node" designates in particular a sensor or an actuator. In a preferred embodiment, the flexible sheet device according to the invention comprises a plurality of nodes 20, 20', for example at least 10 nodes or more. Those nodes need to be powered.

According to the invention, the nodes 20, 20' are advantageously powered with the power from the RF power source 10 in a wireless way via the flexible waveguide. In other words, the flexible waveguide distributes power via guided propagation, by remotely or wirelessly powering the nodes 20, 20'. Therefore, the flexible waveguide acts as power distribution and delivery system.

The RF power source 10 feeds the flexible waveguide without the need of mechanical contacts or wires between the nodes 20, 20' and the RF power source 10, e.g. via the conductive layer(s) 1, 2.

In the embodiment illustrated in FIG. 1, the flexible waveguide forms a bi-dimensional flexible sheet device. In other words, the flexible sheet device 100 extends in the x and y directions, wherein the dimension along the x and y directions are at least one order the magnitude larger than the dimension along the z direction (see FIG. 2 or 3). The flexible sheet device 100 comprises a plurality of nodes 20, 20' that are distributed along the x and y directions (i.e., substantially in the plane of the flexible sheet device within and/or outside the flexible waveguide, see below). The bi-dimensional flexible sheet device 100 is designed so that it can guide the propagation of the power or guide the power generated by the RF power source 10 in the flexible dielectric layer 3, in the x and y directions. Thus the power propagates in two independent propagation the x and y directions such that each node 20, 20' of the plurality of nodes 20, 20' can be powered with the power from the RF power source 10 in a wireless way via the power generated by the RF power source 10 propagating of the flexible dielectric layer 3 in the x and y directions.

Figure 4:
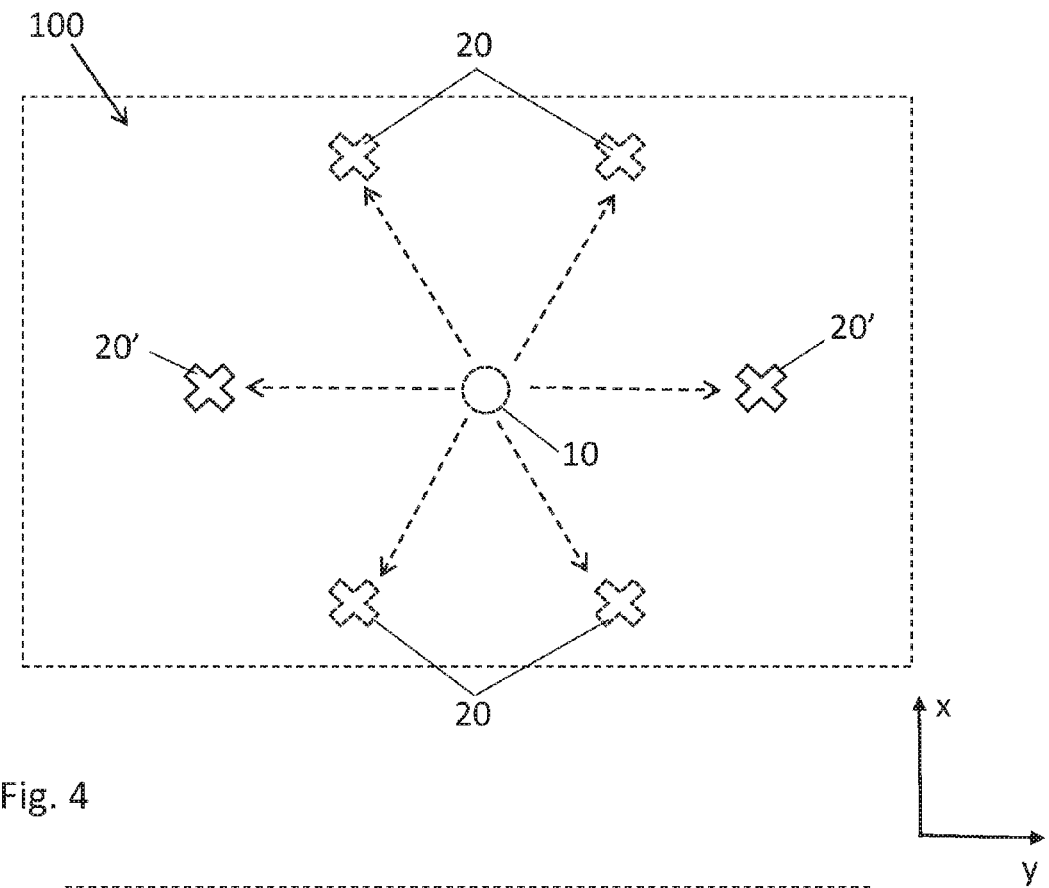
FIG. 4 illustrates an arrangement of the nodes on the flexible waveguide, according to an embodiment.

In an embodiment shown in FIG. 4, the plurality of nodes 20, 20' are arranged on the bi-dimensional flexible sheet device 100 in a starlike network where the nodes 20, 20' are distributed around the RF power source 10.

Figure 5:
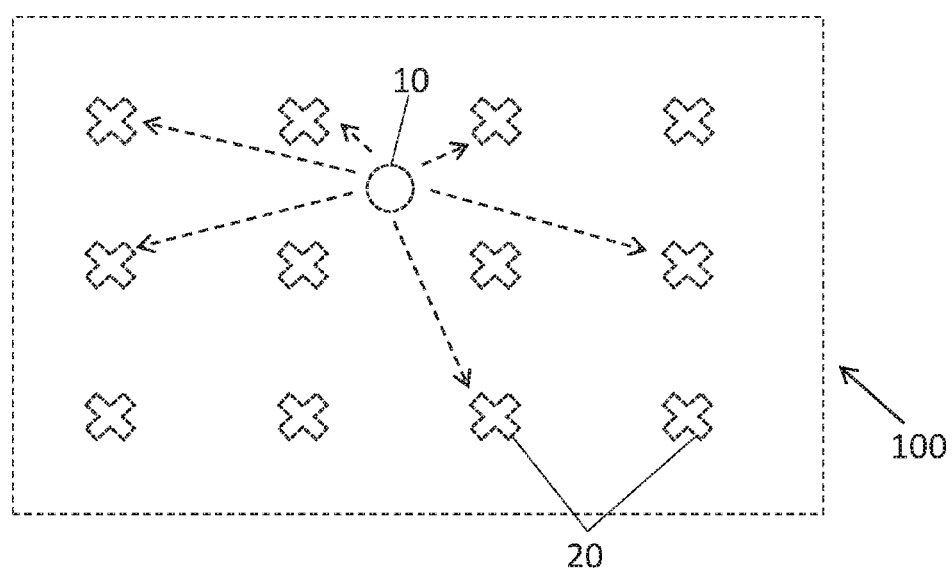
FIG. 5 illustrates an arrangement of the nodes on the flexible waveguide, according to another embodiment

FIG. 5 illustrates another arrangement wherein the plurality of nodes 20, 20' are arranged in a mesh pattern on the bi-dimensional flexible sheet device 100.

The system 100 of the invention allows for increased flexibility in placing the nodes 20, 20' along the x and y directions on the flexible sheet device 100. For instance, the system 100 allows for modifying the placement of the nodes 20, 20', adding and/or removing the nodes 20, 20' on the flexible sheet device 100 and thus, changing the arrangement (or topology) of the nodes 20, 20'. The nodes 20, 20' can be powered by the power generated by the RF power source 10 propagating of the flexible dielectric layer 3 in the x and y directions, independently of their position on the bi-dimensional flexible sheet device 100.

The system according to the invention is then battery-less. It is also robust as mechanical contacts or wires, which can be difficult to implement and could be a source of failure, are absent.

Moreover, the system according to the invention is easy and cheap to manufacture, in particular when a plurality of nodes 20, 20' are present. Finally, the positions of nodes 20, 20' are not constrained by the presence of wires or connections, for powering or communication.

In one preferred embodiment, the nodes 20, 20' comprise a RF/DC power converter (not illustrated) arranged to convert the received RF power from the RF power source 10 to a DC power, which is sent to a DC power supply module (not illustrated) connected to the converter.

In another embodiment, the node 20, 20' is suitable to be powered with RF power of some tens of mW or less.

The layers 1 to 3 of the waveguide are flexible, i.e. they can be bent without breaking. For example, the dielectric layer 3 can be made by flexible plastic substrates, such as polyimide, PET or silicone. The conductive layer can be made e.g. by a flexible copper foil or by a flexible foil comprising a copper alloy or any other flexible metal or alloy. In another embodiment, the conductive layer comprises or it is made of Indium tin oxide (ITO), zinc oxide (ZnO). In another embodiment it comprises or it is made of a coating (i.e. performed by the Aerosol Jet technology) comprising a conductive alloy or any other flexible metal or alloy, or any other non-metallic flexible material having electrical conductivity. In one embodiment, the conductive layer comprises or is made of liquid metal.

In a preferred embodiment, the layers 1 to 3 of the waveguide are also stretchable, i.e. they are made or be capable of being made longer or wider without tearing or breaking. For example the dielectric layer can be made by stretchable materials such as silicones or polyurethanes, and the conductive layer by carbon-based materials.

In another embodiment, they are also elastic, i.e. they can easily return to their original size or shape after being stretched or otherwise deformed.

The flexible sheet device according to the invention can then be easily placed on a target and can conform to the surface of the target thanks to its flexibility. It can take different shapes and various contours depending on the application. It can be rolled on a pipe or tube. Moreover, it can also be stretchable.

In one preferred embodiment, the flexible sheet device is an artificial skin that can be used for prosthetics exoskeletons, tactile service and industrial robots able to work around people, as e.g. cyber skin.

In one preferred embodiment, the flexible sheet device comprises connecting means allowing to perform a mechanical connection, preferably a removable connection, with the target on which it is placed. Examples of such connecting means comprises glue, adhesive, Velcro®, belt, strip, etc.

In one embodiment, if the flexible sheet device according to the invention is not placed on a target, it is substantially flat. In other words, each flexible layer 1 to 3 can be substantially planar when not used on a target.

Examples of sensors 20, 20' of the system according to the invention are temperature sensors, pressure sensors, humidity sensors, position sensors, acceleration sensors, orientation sensors, vibration sensors, stress sensors, etc. They can also use different technologies and be e.g. inductive sensors, capacitive sensors, Hall sensors, magnetoresitive sensors, etc.

Examples of actuators according to the invention are micro-motors, piezoelectric actuators, electroactive polymers, biomorph, camera's actuators, etc.

In the illustrated embodiments, the RF power source 10 is in the flexible dielectric layer 3. However the present invention is not limited to such configuration, and the RF power source 10 can also be placed outside the waveguide. In such a case, the RF power source will be placed in proximity to the flexible waveguide, so that the wireless transmission of the power from RF power source 10 to the flexible waveguide can be efficiently achieved.

In the embodiment of FIG. 2, the node 20 is in the flexible dielectric layer 3, so in the flexible waveguide: in such a case, the node is powered by the power wirelessly conveyed by the flexible waveguide, in particular by its dielectric layer 3.

In the embodiment of FIG. 3, the node 20' is outside the waveguide, e.g. placed on the external surface of the first flexible conductive layer 1. In such a case, the waveguide comprises an antenna 4, distinct from the RF power source 10, for transmitting the RF power from the RF power source 10 to the node 20'. In such a case, the node 20' would be placed at a distance from the antenna 4 allowing the reception by the node 20' of at least the minimum power necessary to the node for working In the embodiment of FIG. 3, the antenna 4 is a slot antenna formed in the conductive layer 1 of the waveguide. In this case, the slot antenna consists of a conductive surface, e.g. the surface of the conductive layer 1 or 2, comprising a hole or slot 5 cut out. As knows, the shape and size of the hole or slot 5, as well as the driving frequency, determine the radiation distribution pattern of the antenna 4.

Although in FIG. 3 the antenna 4 is formed only on the first conductive layer 1, the present invention is not limited to such embodiment and one or more antenna can be present on the second conductive layer 2 only or on both conductive layers 1, 2.

As the conductive layers 1, 2 are flexible, the antenna 4 will be flexible as well. If the conductive layers 1, 2 are also stretchable and/or elastic, the antenna 4 will be stretchable and/or elastic as well.

In one preferred embodiment, the conductive layers 1 or 2 according to the invention comprise more than one antenna 4.

The system according to the invention can comprise both nodes 20 inside the flexible dielectric layer 3, and nodes 20' outside the flexible dielectric layer 3, as illustrated in FIG. 1.

The system according to the invention is easy to use: in a preferred embodiment, it comprises sensors and/or actuators and their power source, it does not need any other device for work, it can be easily placed on a target and conform to its surface. Sensors can then collect data for the specific application.

The present invention concerns also a method for remote powering at least one sensor or actuator 20 from a RF power source 10, comprising generating a RF power from the RF power source 10 wirelessly coupled to a flexible waveguide, the flexible waveguide comprising a flexible dielectric layer 3 and at least one flexible conductive layer 1 or 2, guiding the propagation of the RF power or guiding the RF power from the RF power source 10 to the at least one sensor or actuator 20, the at least one sensor or actuator being coupled to the flexible waveguide, receiving the RF power by at least one sensor or actuator 20, and powering at least one sensor or actuator 20 by using the RF power, e.g. by converting the RF power to DC power.

The present invention concerns also the use of a flexible waveguide comprising a flexible dielectric layer 3 and at least one flexible conductive layer 1, 2, for guiding the propagation of a RF power or guiding the RF power from a RF power source 10 arranged to be wirelessly coupled to the flexible waveguide, to at least one sensor or actuator 20 arranged to be coupled to the flexible waveguide, in order to wirelessly power this sensor or actuator 20.

REFERENCE NUMBERS AND SIGNS USED IN THE FIGURES

1 First flexible conductive layer
2 Second flexible conductive layer
3 Flexible dielectric layer
4 Antenna
5 Hole or slot
10 RF power source
20 Node inside the waveguide
20' Node outside the waveguide
100 System
e1 Thickness of the first flexible conductive layer
e2 Thickness of the second flexible conductive layer
e3 Thickness of the dielectric layer

The invention claimed is:

1. A system for remote powering at least one sensor or actuator from a RF power source, comprising
a flexible waveguide comprising
a flexible dielectric layer and at least one flexible conductive layer connected to said flexible dielectric layer,
said at least one sensor or actuator, arranged to be coupled to said flexible waveguide,
said RF power source, arranged to be wirelessly coupled to said flexible waveguide and to generate RF power,
the flexible waveguide guiding the propagation of said RF power from said RF power source to said at least one sensor or actuator in order to wirelessly power said at least one sensor or actuator,
wherein said RF power source is placed in the flexible dielectric layer, such that it is inside the flexible waveguide.

2. The system of claim 1, said flexible waveguide forming a flexible sheet device being configured to be placed on a target.

3. The system of claim 1, said at least one sensor or actuator being in the flexible dielectric layer.

4. The system of claim 1, said at least one sensor or actuator being outside the waveguide, the waveguide comprising an antenna for transmitting the RF power from said RF power source to said sensor or actuator.

5. The system of claim 1, the flexible waveguide comprising an antenna being a slot antenna formed in the conductive layer.

6. The system of claim 1, comprising two conductive layers, the dielectric layer being between the first conductive layer and the second conductive layer.

7. The system of claim 1, the sensor or actuator comprising a RF/DC power converter and a DC power supply module connected to said converter.

8. The system of claim 1, the sensor or actuator being arranged to be powered with RF power of some tens of mW or less.

9. The system of claim 1, the thickness of the flexible waveguide being less than 5 mm, e.g. 1 mm.

10. The system of claim 1, the dielectric layer and/or the metallic layer(s) being stretchable and/or elastic.

11. The system of claim 1,
wherein said flexible waveguide forms a bi-dimensional flexible sheet device comprising a plurality of sensors or actuators distributed along the two directions of the bi-dimensional flexible sheet device; the flexible sheet device being configured such that each sensor or actuator of the plurality of sensors or actuators is powered by the power generated by the RF power source and guided along the two directions of the bi-dimensional flexible sheet device.

12. A method for remote powering at least one sensor or actuator from a RF power source using a system according to claim 1, wherein the method comprises the steps of:
generating a RF power from said RF power source, said RF power source being wirelessly coupled to a flexible waveguide, said flexible waveguide comprising a flexible dielectric layer and at least one flexible conductive layer
guiding the propagation of said RF power from said RF power source to said at least one sensor or actuator, said at least one sensor or actuator being coupled to said flexible waveguide
receiving said RF power by said at least one sensor or actuator and
powering said at least one sensor or actuator by using said RF power, e.g. by converting said RF power to DC power.

13. The system of claim 1, wherein the flexible sheet comprises an artificial skin suitable for prosthetics exoskeletons, tactile service and industrial robots.

14. The system of claim 2, being standalone and self-standing.

15. The system of claim 2,
wherein said flexible sheet device is configured to be placed on a receiving device.

16. The system of claim 2,
wherein the flexible sheet device comprises a connecting means allowing to perform a mechanical connection between the flexible sheet device and the receiving device.

17. The system of claim 2,
wherein the flexible sheet comprises an artificial skin suitable for prosthetics exoskeletons, tactile service and industrial robots.

18. The system of claim 2, wherein the flexible sheet device comprises a connecting means allowing to perform a mechanical connection on the target.

* * * * *